US012636102B2

(12) United States Patent
Meglan

(10) Patent No.: US 12,636,102 B2
(45) Date of Patent: May 26, 2026

(54) SYSTEM FOR CHECKING INSTRUMENT STATE OF A SURGICAL ROBOTIC ARM

(71) Applicant: Covidien LP, Mansfield, MA (US)

(72) Inventor: Dwight Meglan, Westwood, MA (US)

(73) Assignee: Covidien LP, Mansfield, MA (US)

( * ) Notice: Subject to any disclaimer, the term of this patent is extended or adjusted under 35 U.S.C. 154(b) by 450 days.

(21) Appl. No.: 17/783,456

(22) PCT Filed: Nov. 10, 2020

(86) PCT No.: PCT/US2020/059789
§ 371 (c)(1),
(2) Date: Jun. 8, 2022

(87) PCT Pub. No.: WO2021/118733
PCT Pub. Date: Jun. 17, 2021

(65) Prior Publication Data
US 2023/0024362 A1     Jan. 26, 2023

Related U.S. Application Data

(60) Provisional application No. 62/945,367, filed on Dec. 9, 2019.

(51) Int. Cl.
| | |
|---|---|
| *A61B 34/35* | (2016.01) |
| *A61B 34/00* | (2016.01) |
| *A61B 34/20* | (2016.01) |
| *A61B 34/37* | (2016.01) |
| *B25J 9/16* | (2006.01) |

(52) U.S. Cl.
CPC .............. *A61B 34/35* (2016.02); *A61B 34/20* (2016.02); *A61B 34/25* (2016.02); *A61B 34/37* (2016.02);
(Continued)

(58) Field of Classification Search
CPC ......... A61B 34/35; A61B 34/20; A61B 34/25; A61B 34/37; A61B 2034/2057;
(Continued)

(56) References Cited

U.S. PATENT DOCUMENTS

| | | | |
|---|---|---|---|
| 2014/0128885 A1 | 5/2014 | Dachs, II et al. | |
| 2015/0265347 A1* | 9/2015 | Yates ................. | A61B 18/1445 |
| | | | 606/50 |

(Continued)

FOREIGN PATENT DOCUMENTS

| | | |
|---|---|---|
| CN | 104736094 A | 6/2015 |
| CN | 105095918 A | 11/2015 |

(Continued)

OTHER PUBLICATIONS

International Search Report and Written Opinion dated Mar. 4, 2021 issued in corresponding PCT Appln. No. PCT/US2020/059789.
(Continued)

*Primary Examiner* — Dylan M Katz
(74) *Attorney, Agent, or Firm* — Carter, DeLuca & Farrell, LLP

(57) ABSTRACT

A surgical robotic system includes: a surgical console having a display and a user input device configured to generate a user input and a surgical robotic arm having a surgical instrument configured to treat tissue and being actuatable in response to the user input; and a video camera configured to capture video data that is displayed on the display. The system also includes a control tower coupled to the surgical console and the surgical robotic arm. The control tower is configured to: process the user input to control the surgical instrument and to record the user input as input data; train a machine learning system using the input data and the video data; and execute the at least one machine learning system to determine probability of failure of the surgical instrument.

18 Claims, 6 Drawing Sheets

(52) U.S. Cl.
CPC .............. *B25J 9/161* (2013.01); *B25J 9/163* (2013.01); *A61B 2034/2057* (2016.02); *A61B 2034/2065* (2016.02)

(58) Field of Classification Search
CPC .. A61B 2034/2065; A61B 2018/00988; A61B 2034/2055; A61B 2034/2074; A61B 90/08; A61B 2090/0803; A61B 2090/0804; A61B 2090/0809; A61B 90/37; A61B 34/30; B25J 9/161; B25J 9/163; B25J 9/1689; B25J 19/023; B25J 19/061; B25J 19/0095; G05B 2219/45119
See application file for complete search history.

(56) References Cited

U.S. PATENT DOCUMENTS

| | | |
|---|---|---|
| 2017/0031329 A1 | 2/2017 | Inagaki et al. |
| 2018/0055577 A1 | 3/2018 | Barral et al. |
| 2019/0069957 A1* | 3/2019 | Barral .................... A61B 34/20 |
| 2019/0265657 A1 | 8/2019 | Inagaki et al. |
| 2019/0374292 A1* | 12/2019 | Barral .................... B25J 9/1682 |
| 2020/0038109 A1* | 2/2020 | Steinberg .............. G16H 50/50 |

FOREIGN PATENT DOCUMENTS

| | | |
|---|---|---|
| CN | 106030683 A | 10/2016 |
| CN | 107436595 B | 12/2017 |

OTHER PUBLICATIONS

Chinese Office Action issued in corresponding Chinese Application No. 202080080863.8 mailed Mar. 12, 2025, together with English language translation retrieved from the Global Dossier.

* cited by examiner

Video
Data

Data
Logs

Sensor
Data

Service Life
Data

Procedure
Data

100

Learning
System

FIG. 5

SYSTEM FOR CHECKING INSTRUMENT STATE OF A SURGICAL ROBOTIC ARM

CROSS REFERENCE TO RELATED APPLICATIONS

The present application is a National Stage Application under 35 U.S.C. § 371(a) of PCT/US2020/059789, filed Nov. 10, 2020, which claims the benefit of and priority to U.S. Patent Provisional Application No. filed 62/945,367 filed on Dec. 9, 2019. The entire disclosures of the foregoing applications are incorporated by reference herein.

BACKGROUND

Surgical robotic systems are currently being used in minimally invasive medical procedures. Some surgical robotic systems may include a surgical console controlling a surgical robotic arm and a surgical instrument having an end effector (e.g., forceps or grasping instrument) coupled to and actuated by the robotic arm.

Certain robotic surgical procedures utilize instruments, such as electrosurgical instruments. Such instruments are capable of rapid and effective completion of tissue manipulation tasks. The instruments are highly complex and include electrical components as well as mechanical linkages and actuators that are disposed in confined spaces. However, the instruments are susceptible to failure due to compromised structural integrity, which can cause unexpected and even detrimental results. In particular, the materials used to electrically isolate components of these types of instruments can be prone to damage, which may not be readily apparent to the surgeon using the robot.

Accordingly, there is a need for a system that is configured to automatically detect presence of such damage in the surgical instruments and disable one or more functions or components of the instrument upon detection of failure, thereby avoiding potential complication from using the damaged instrument.

SUMMARY

The present disclosure provides a surgical robotic system including a machine learning algorithm executable by a controller, which allows the system to determine an operational status of a surgical instrument, including remaining usable life of the surgical instrument or whether the surgical instrument is about to be damaged from overuse. Through the use of machine learning, the system is configured to identify service life parameters of the surgical instrument (e.g., predicted use in time and/or number of actuations), whether a surgical instrument is damaged, and/or characteristics and patterns representative of damaged instruments. If the processor using the machine learning algorithm identifies presence of any damage in the surgical instrument or predicts that the surgical instrument is about to be damaged, e.g., subsequent actuation of the surgical instrument would result the instrument, then the processor disables activation of surgical instrument as well as indicates the problem to the clinician.

The system is configured to continuously predict or determine the operational status of the surgical instrument. In particular, the system is configured to discern on a continual basis during a procedure whether the surgical instrument can perform its intended function. The system may monitor the operational status of any surgical instrument including mechanical instruments, such as graspers, staplers, clip appliers, and the like, and electrosurgical instruments, such as electrosurgical forceps, dissectors, coagulators, to discern if there are mechanical and/or electrical failures. This could be facilitated by adding in measurement of clinician commanded movements relative to tool actual movements as an input to training the neural network.

The machine learning algorithm may be trained using video of the surgical tools as well as any other data sources available from the robotic system such as the electrical performance of the electrosurgical tools over the course of their service life as well as during the present procedure. In addition, data pertaining to the surgical procedure, e.g., presurgical plan, from the system may be combined with the above to produce additional insights e.g., training, into the behavior of the surgical instruments based on their actual usage patterns. The algorithm may factor individual surgical instrument parameters based on actual usage patterns differently over the expected service life of each surgical instrument.

According to one embodiment of the present disclosure, a surgical robotic system is disclosed. The surgical robotic system includes: a surgical console having a display and a user input device configured to generate a user input and a surgical robotic arm having a surgical instrument configured to treat tissue and being actuatable in response to the user input; and a video camera configured to capture video data that is displayed on the display. The system also includes a control tower coupled to the surgical console and the surgical robotic arm. The control tower is configured to: process the user input to control the surgical instrument and to record the user input as input data; train a machine learning system using the input data and the video data; and execute the at least one machine learning system to determine probability of failure of the surgical instrument.

According to one aspect of the above embodiment, the at least one machine learning system is a neural network. The neural network may be trained using at least one of supervised training, unsupervised training, or reinforcement learning. The machine learning system is configured to compare the probability of failure of the surgical instrument to a threshold. The machine learning system may be further configured to output at least one of an audio or video indication in response to the probability of failure of the surgical instrument exceeding the threshold. The machine learning system may be also configured to disable the surgical instrument in response to the probability of failure of the surgical instrument exceeding the threshold.

According to another embodiment of the present disclosure, a surgical robotic system is disclosed. The surgical robotic system includes: a surgical console having a display and a user input device configured to generate a user input and a surgical robotic arm having a surgical instrument configured to treat tissue and being actuatable in response to the user input; a sensor configured to measure at least one parameter of the surgical instrument and to output sensor data; and a video camera configured to capture video data that is displayed on the display. The system also includes a control tower coupled to the surgical console and the surgical robotic arm. The control tower is configured to: process the user input to control the surgical instrument and to record the user input as input data; train a machine learning system using the input data, the sensor data, and the video data; and execute the machine learning system to determine probability of failure of the surgical instrument.

According to one aspect of the above embodiment, the control tower is further configured to process the user input to control the surgical instrument and to record the user input as input data.

According to another aspect of the above embodiment, the machine learning system is a neural network. The neural network may be trained using at least one of supervised training, unsupervised training, or reinforcement learning. The machine learning system may be configured to compare the probability of failure of the surgical instrument to a threshold. The machine learning system may be further configured to output at least one of an audio or video indication in response to the probability of failure of the surgical instrument exceeding the threshold. The machine learning system may be also configured to disable the surgical instrument in response to the probability of failure of the surgical instrument exceeding the threshold.

According to a further aspect of the above embodiment, a method for controlling a surgical robotic system is disclosed. The method includes: generating a user input through a user input device of a surgical console and recording input data; processing the user input to generate a movement command at a control tower coupled to the surgical console; and transmitting the movement command to a surgical robotic arm, the surgical robotic arm including a surgical instrument configured to treat tissue and being actuatable in response to the user input. The method further includes: capturing video data through a video camera disposed on the surgical robotic arm; measuring using a sensor at least one parameter of the surgical instrument to output sensor data; training a machine learning system using the input data, the sensor data, and the video data; and executing the machine learning system to determine probability of failure of the surgical instrument.

According to one aspect of the above embodiment, the machine learning system is a neural network.

According to another aspect of the above embodiment, the method further includes training the neural network using at least one of supervised training, unsupervised training, or reinforcement learning.

According to a further aspect of the above embodiment, the method further includes comparing the probability of failure of the surgical instrument to a threshold. The method also includes outputting at least one of an audio or video indication in response to the probability of failure of the surgical instrument exceeding the threshold. The method further includes disabling the surgical instrument in response to the probability of failure of the surgical instrument exceeding the threshold.

BRIEF DESCRIPTION OF THE DRAWINGS

Embodiments of the present disclosure are described herein with reference to the accompanying drawings, wherein:

FIG. 5 is a schematic diagram of a machine learning system implemented in the surgical robotic system of FIG. 1.

DETAILED DESCRIPTION

Figure 1:
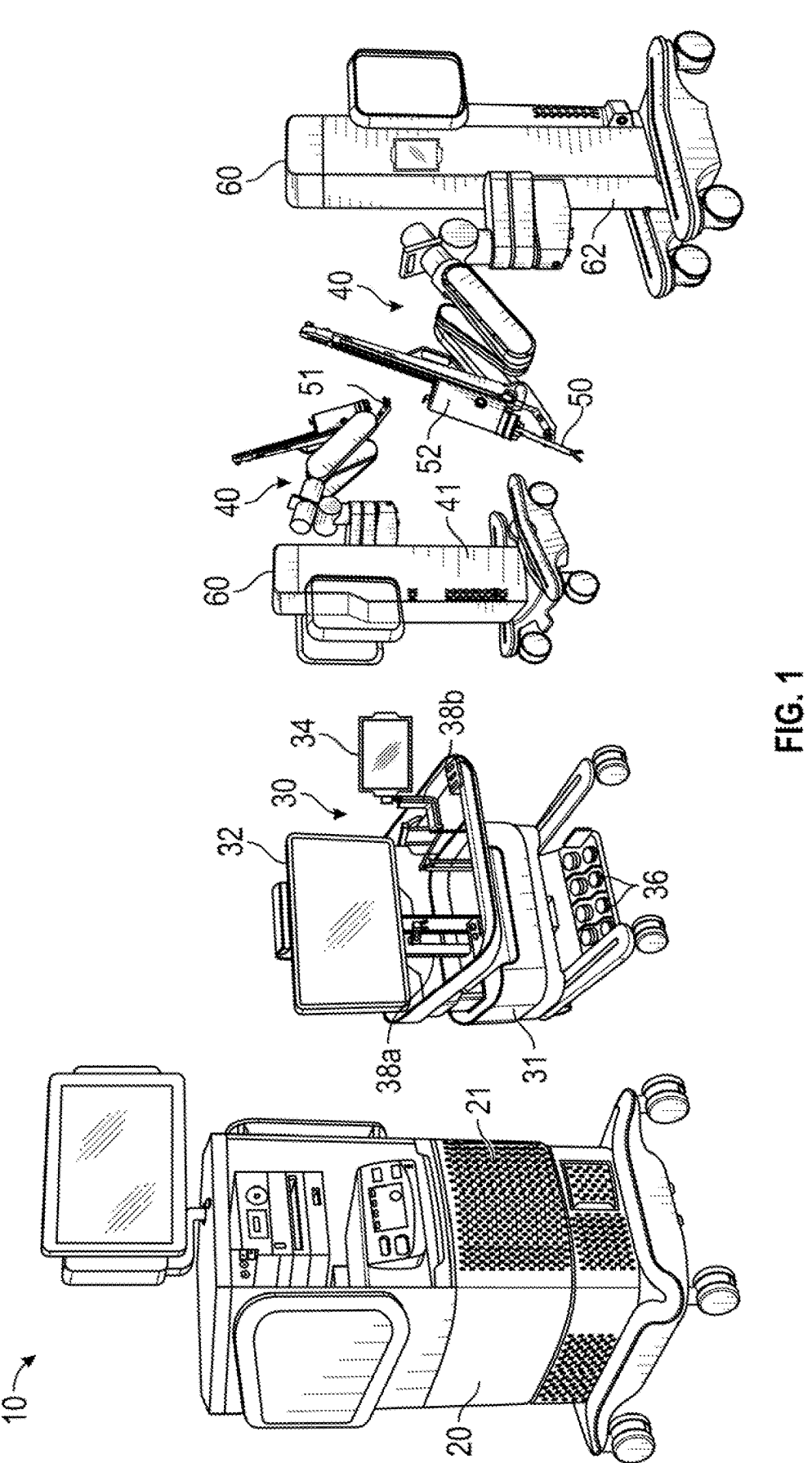
FIG. 1 is a schematic illustration of a surgical robotic system including a control tower, a console, and one or more surgical robotic arms according to the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

As will be described in detail below, the present disclosure is directed to a surgical robotic system, which may include a surgical console, a control tower, and one or more mobile carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

The terms "artificial intelligence," "data models," or "machine learning" may include, but are not limited to, neural networks, convolutional neural networks (CNN), recurrent neural networks (RNN), generative adversarial networks (GAN), Bayesian Regression, Naive Bayes, nearest neighbors, least squares, means, and support vector regression, among other data science and artificial science techniques.

The term "application" may include a computer program designed to perform functions, tasks, or activities for the benefit of a clinician. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 may also be coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope configured to provide a video feed for the clinician. In further embodiments, the surgical instrument 50 may be an electrosurgical forceps configured to seal tissue by compression tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

Each of the robotic arms 40 may include a camera 51 configured to capture video of the surgical site. The camera 51 may be a stereoscopic camera and may be disposed along with the surgical instrument 50 on the robotic arm 40. The surgical console 30 includes a first display 32, which displays a video feed of the surgical site provided by camera 51 of the surgical instrument 50 disposed on the robotic arms 40, and a second display device 34, which displays a user interface for controlling the surgical robotic system 10. The surgical console 30 also includes a plurality of user interface devices, such as foot pedals 36 and a pair of handle controllers 38a and 38b which are used by a clinician to remotely control robotic arms 40.

The control tower 20 acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
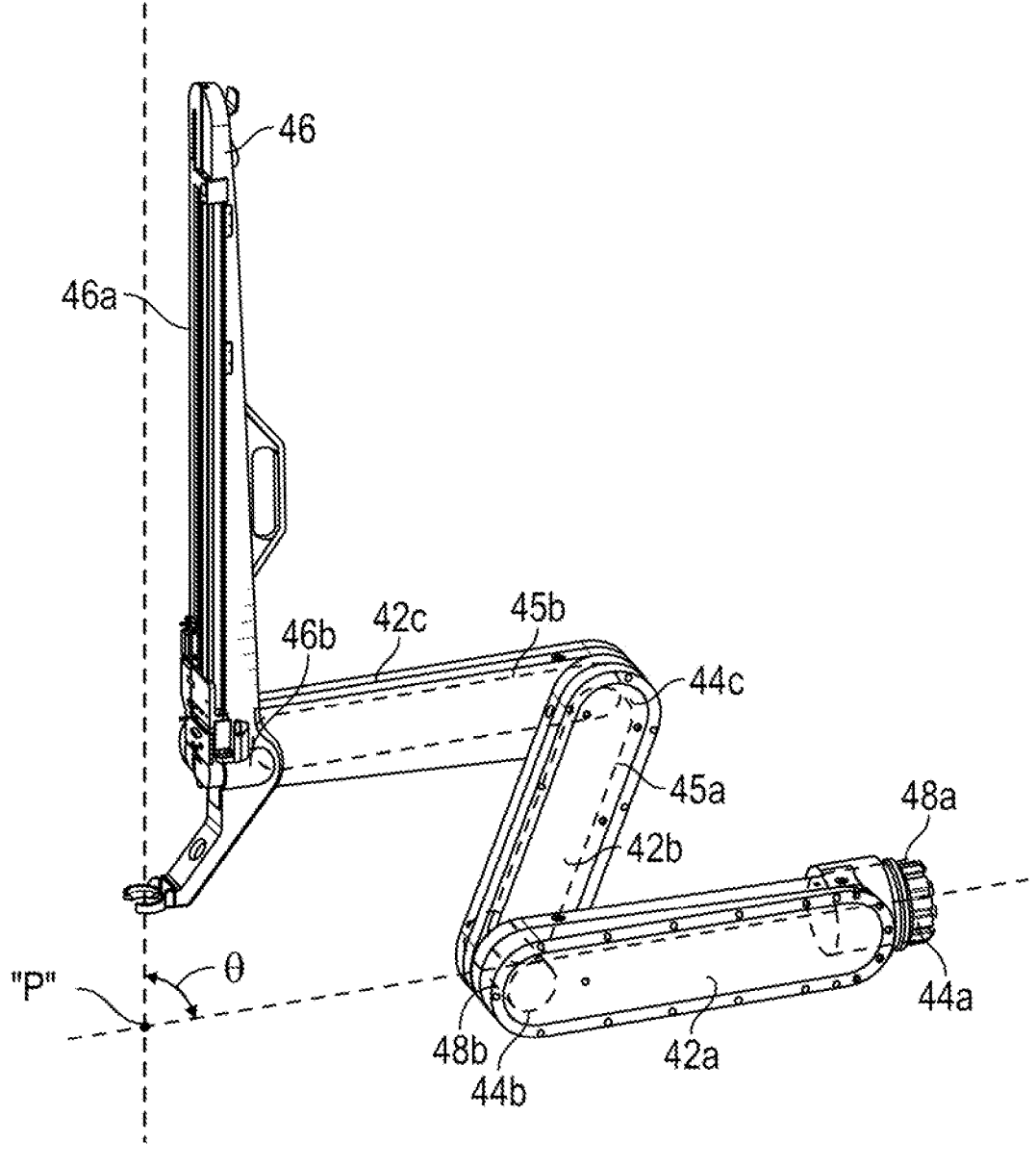
FIG. 2 is a perspective view of a surgical robotic arm of the surgical robotic system of FIG. 1 according to the present disclosure.
Figure 3:
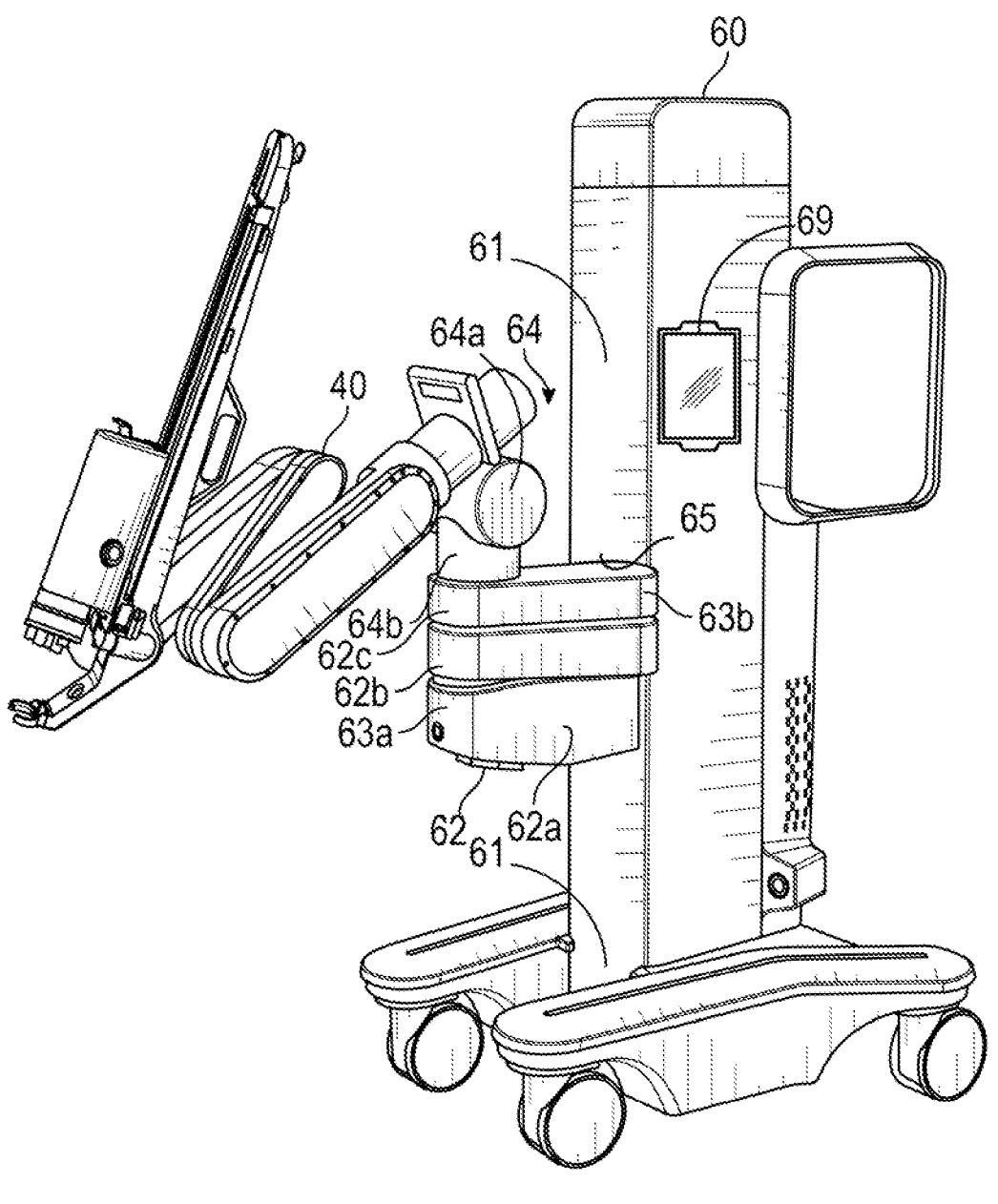
FIG. 3 is a perspective view of a setup arm with the surgical robotic arm of the surgical robotic system of FIG. 1 according to the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an instrument drive unit 52 (FIG. 1) of the surgical instrument 50, which is configured to couple to an actuation mechanism of the surgical instrument 50. Instrument drive unit 52 transfers actuation forces from its actuators to the surgical instrument 50 to actuate components (e.g., end effectors) of the surgical instrument 50. The holder 46 includes a sliding mechanism 46a, which is configured to move the instrument drive unit 52 along the second longitudinal axis defined by the holder 46. The holder 46 also includes a joint 46b, which rotates the holder 46 relative to the link 42c.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
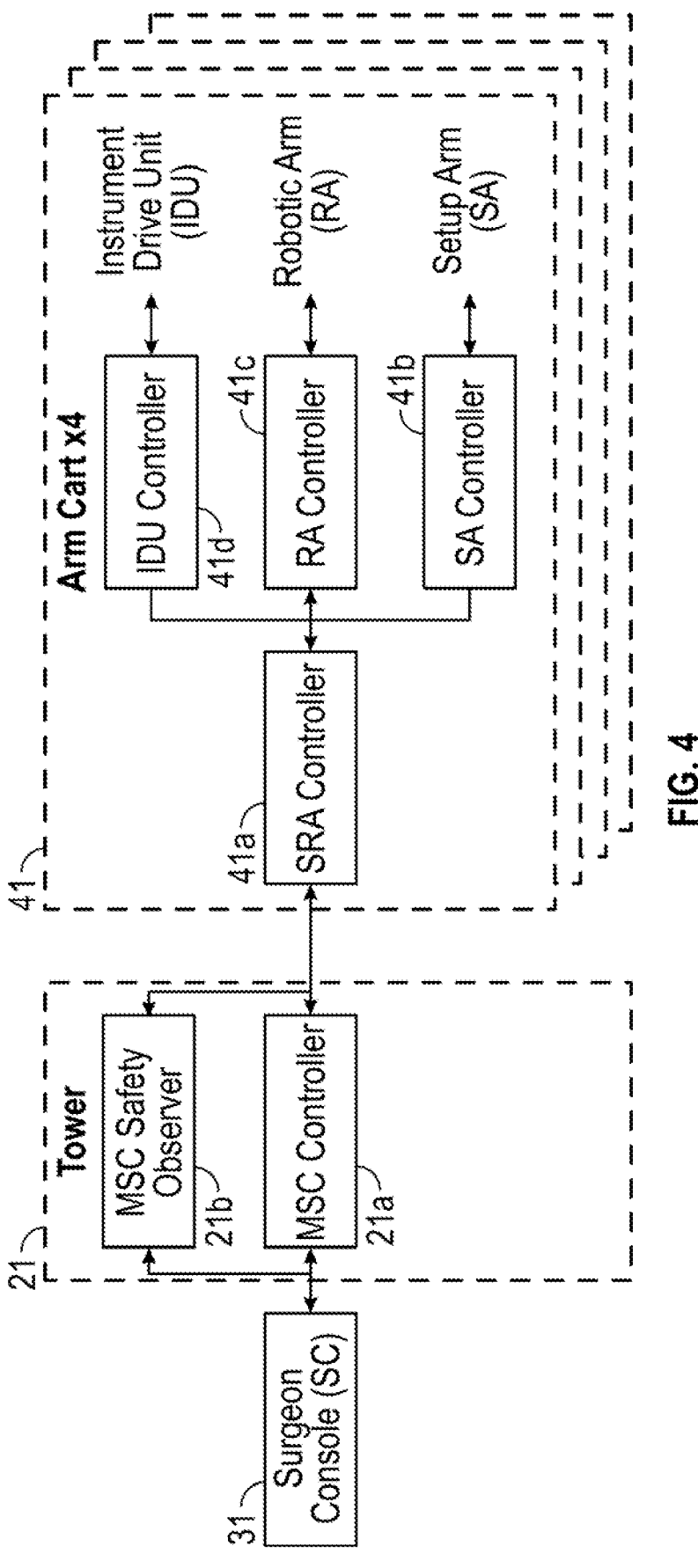
FIG. 4 is a schematic diagram of a computer architecture of the surgical robotic system of FIG. 1 according to the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the instrument drive unit 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the instrument drive unit 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the instrument drive unit 52. The IDU controller 41d calculates actual angles based on the motor positions and transmits the actual angles back to the main cart controller 41a.

Figure 5:
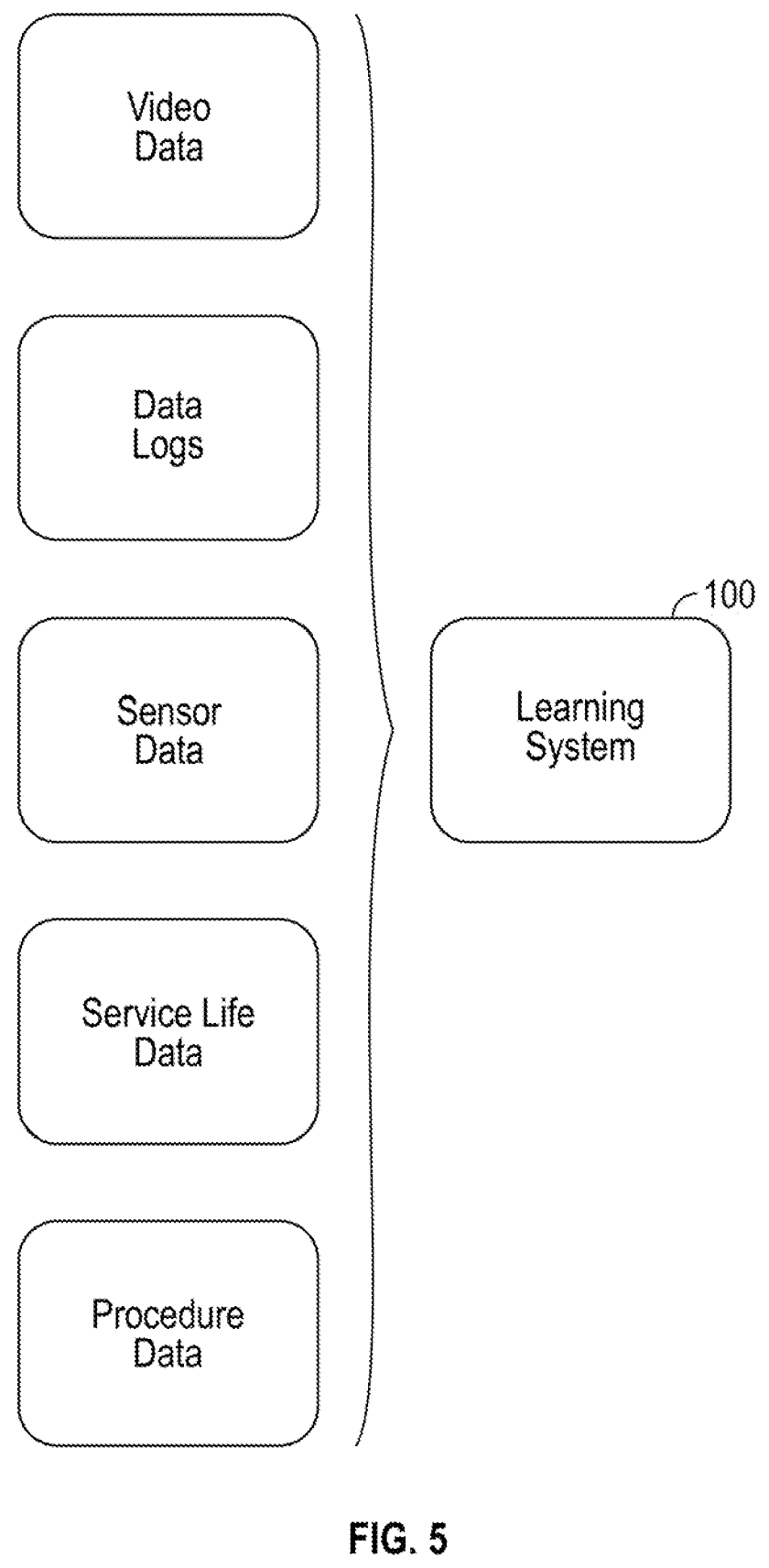

With reference to FIG. 5, the surgical robotic system 10 includes a learning system 100 which may be a neural network. In various embodiments, the neural network may include a temporal convolutional network, with one or more fully connected layers, or a feed forward network. In various embodiments, training of the neural networks may happen on a separate system, e.g., graphic processor unit ("GPU") workstations, high performing computer clusters, etc., and the trained networks would then be deployed in the surgical robotic system 10. In further embodiments, training of the neural networks may happen locally, i.e., on the computer 21.

The learning system 100 may be trained on video streams, which may be recorded input video data from the camera(s) 51 of the system 10, such as those captured from previous procedures. In addition, the learning system 100 may be trained on sensor data from the surgical instrument 50, the robotic arm 40, or from any other component of the system 10 as well as data logs, including input commands from the surgical console 30. Furthermore, the video and sensor data may be combined with procedure data, which may include annotations of specific actions undertaken by the clinician during a procedure. The annotations may be generated manually and/or automatically by using a secondary neural network. More specifically, the secondary neural network may be used to identify and annotate video data and/or sensor data to generate procedure data.

Furthermore, the learning system 100 may be trained using service life data for surgical instruments 50. Service life data of the surgical instruments 50 may be stored locally on the surgical instrument 50, the robotic arm 40, the control tower 20, and/or the surgical console 30. This cumulative data set, which includes the video data, the sensor data, the procedure data, and the service life data, is used to train the learning system 100 to detect probability of fault for surgical instrument 50. Once trained, the learning system 100 may be embodied as an application or software executable by the computer 21 of the control tower 20.

The learning system 100 operates at a low latency and is configured to inform the clinician that something may be wrong with the surgical instrument 100 as soon as it is detected by displaying a warning on the first display 32 of the surgical console 30. In embodiments, the warnings may also be displayed on a display of the control tower 20. This may be done simultaneously with the warnings displayed on the first display 32 or only on the controller tower 20, such that the clinician using the surgical console 30 is not inundated with warnings. This would enable assistants to cross-check the warning before informing the clinician. This configuration would also allow for training the learning system 100 without fully deploying the learning system 100 on the surgical console 30. Once the learning system 100 has been sufficiently trained, such that the false positive rate is acceptable, the learning system 100 may then be deployed to provide alerts to the surgical console 30 as well.

In embodiments, in addition to identifying the operational status of the surgical instrument 50 and output the same to the system 10, the learning system 100 may also deactivate one or more functions of the surgical instrument 50 that are affected by the operational status. Thus, in embodiments where the surgical instrument 50 is an electrosurgical instrument, the learning system 100 may turn off the ability to activate surgical energy and to inform the surgeon that something have gone wrong with the surgical instrument. The surgeon may decide how to proceed may continue to use the surgical instrument 50 even without its electrosurgical capabilities.

Figure 6:
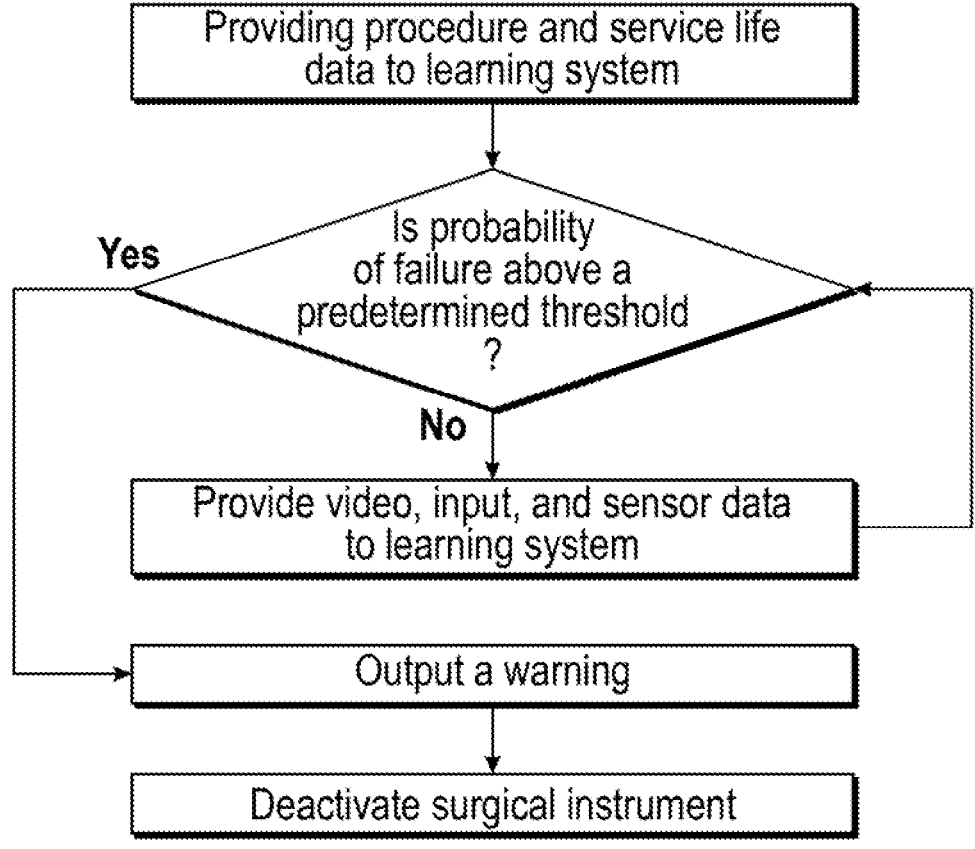
FIG. 6 is a flow chart of a method according to the present disclosure utilizing algorithm based on the machine learning system of FIG. 5.

With reference to FIG. 6, a method implementing the learning system 100 into the workflow of the system 10 is disclosed. The system 10 utilizes the learning system 100, once it has been trained, to determine an operational status of the surgical instrument 50 being used during the surgical procedure. In particular, the computer 21 of the control tower 20 executes the learning system 100, which includes a set of criteria indicating failure of the surgical instrument 50. The learning system 100 receives as input the following real-time data: video data, sensor data, user input data, service life data, and procedure data. This data is similar to the data used to train the learning system 100.

The video data is received from the camera 51 and may be processed in real-time by the learning system 100. Similarly, the sensor data may be transmitted by the surgical instrument 50 to the learning system 100. User input data is provided to the learning system 100 by the surgical console 30 contemporaneously with the inputs being transmitted to the robotic arm 40 and the surgical instrument 50. Procedure data may be loaded into the control tower 20 prior to commencement of the surgical procedure. Service life data may be stored on the surgical instrument 50 (e.g., a storage device disposed within the surgical instrument 50). In embodiments, the service life data may be stored in a remote or local database accessible by the control tower 20. The learning system 100 may access the service data from any of these sources prior to commencement of the procedure. Thus, initially the learning system 100 analyzes procedure data and service life data since this data is available at the outset and is not updated during the procedure.

The learning system 100 determines a failure probability of each of the surgical instruments 50 being used in the system 10. In particular, the learning system 100 calculates a probability of failure prior to commencing the surgical instrument 50. If the probability of failure is above a predetermined threshold, which may be about 10%, then the learning system 100 outputs a warning on the first display 32 of the surgical console 30 and/or on a display of the control tower 20.

The other data sources, namely, video data, sensor data, and input data are fed to the learning system 100 during the procedure. During the procedure, the learning system 100 utilizes the formulated criteria during training of the learning system 100, to determine whether the surgical instrument 50 is about to fail and/or has failed with the procedure data and the service life data being used as a baseline. In embodiments, the learning system 100 is configured to determine that there is a high degree of probability (e.g., the threshold of about 10%) that the surgical instrument 50 may fail solely based on the service life data and the procedure data. In which case, the learning system 100 would instruct the system 10 to output an alert to the system 10, namely, on the control tower 20 and/or the surgical console 30. In addition, the learning system 100 may also instruct the system 10 to partially or fully deactivate the surgical instrument 10. Partial deactivation includes disabling one or more of the functions of the surgical instrument 50. In embodiments, partial deactivation may include disabling only the components identified by the learning system 100 as likely to fail. Thus, components which are predicted to continue to function would not be disabled.

The continuous feed of video data, sensor data, and input is also used during the procedure to determine additional criteria indicative of an increased probability of failure of the surgical instrument 50. The combined data stream is used by the learning system 100 to determine the probability of failure of the surgical instrument 50. The probability of failure is determined continuously and is compared to a predetermined threshold, which may be about 10%. If the calculated probability is above threshold, then the learning system 100 outputs a warning on the first display 32 of the surgical console 30 and/or on a display of the control tower 20.

The learning system 100 may be used to predict probability of failure for any surgical instrument 50 including electrosurgical instruments, such as, vessel sealers, dissectors, and coagulators and mechanical instruments, such as graspers, staplers, clip appliers, and the like. Thus, with respect to electrosurgical instruments the learning system 100 may only disable components responsible for transmitting electrical current for treating tissue to prevent electrocuting the patient, while allowing for movement of the surgical instrument 50. With respect to mechanical instruments, the learning system 100 may only disable cutting components and/or stapling components, while allowing the surgical instrument 50 to be moved.

The conditions used by the learning system 100 to determine that the surgical instrument 50 is recorded by the system 10, which may be used for documentation and/or for future refinement of use of the surgical instrument 50 as well as for additional training of the learning system 100.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
   a surgical console including a display and a user input device configured to generate a user input;
   a surgical robotic arm including a surgical instrument configured to treat tissue and being actuatable in response to the user input;
   a video camera configured to capture video data that is displayed on the display; and
   a control tower coupled to the surgical console and the surgical robotic arm, the control tower including a computer and configured to:
   process the user input to control the surgical instrument and to record the user input as input data;
   train locally on the computer at least one machine learning system using the input data and annotated video data, wherein the annotated video data is generated by annotating the video data using procedure data;
   execute the at least one machine learning system in real time to determine probability of failure of the surgical instrument; and
   display a warning on at least one of the display of the surgical console or a display of the control tower in response to probability of failure of the surgical instrument exceeding a threshold.

2. The surgical robotic system according to claim 1, wherein the at least one machine learning system is a neural network.

3. The surgical robotic system according to claim 2, wherein the neural network is trained using at least one of supervised training, unsupervised training, or reinforcement learning.

4. The surgical robotic system according to claim 1, wherein the at least one machine learning system is configured to compare the probability of failure of the surgical instrument to a threshold.

5. The surgical robotic system according to claim 4, wherein the at least one machine learning system is further configured to output at least one of an audio or video indication in response to the probability of failure of the surgical instrument exceeding the threshold.

6. The surgical robotic system according to claim 5, wherein the at least one machine learning system is further configured to disable the surgical instrument in response to the probability of failure of the surgical instrument exceeding the threshold.

7. A surgical robotic system comprising:

a surgical console including a display and a user input device configured to generate a user input;

a surgical robotic arm including:

a surgical instrument configured to treat tissue and being actuatable in response to the user input; and a sensor configured to measure at least one parameter of the surgical instrument and to output sensor data;

a video camera configured to capture video data that is displayed on the display; and a control tower coupled to the surgical console and the surgical robotic arm, the control tower including a computer and configured to:

process the user input to control the surgical instrument and to record the user input as input data;

train at least one machine learning system using the input data, the sensor data, and annotated video data, wherein the annotated video data is generated by annotating the video data using procedure data;

execute the at least one machine learning system in real time to determine probability of failure of the surgical instrument; and display a warning on at least one of the display of the surgical console or a display of the control tower in response to probability of failure of the surgical instrument exceeding a threshold.

8. The surgical robotic system according to claim 7, wherein the at least one machine learning system is a neural network.

9. The surgical robotic system according to claim 8, wherein the neural network is trained using at least one of supervised training, unsupervised training, or reinforcement learning.

10. The surgical robotic system according to claim 7, wherein the at least one machine learning system is configured to compare the probability of failure of the surgical instrument to a threshold.

11. The surgical robotic system according to claim 10, wherein the at least one machine learning system is further configured to output at least one of an audio or video indication in response to the probability of failure of the surgical instrument exceeding the threshold.

12. The surgical robotic system according to claim 11, wherein the at least one machine learning system is further configured to disable the surgical instrument in response to the probability of failure of the surgical instrument exceeding the threshold.

13. A method for controlling a surgical robotic system, the method comprising:

generating a user input through a user input device of a surgical console and recording input data;

processing the user input to generate a movement command at a control tower coupled to the surgical console;

transmitting the movement command to a surgical robotic arm, the surgical robotic arm including a surgical instrument configured to treat tissue and being actuatable in response to the user input;

capturing video data through a video camera;

measuring using a sensor at least one parameter of the surgical instrument to output sensor data;

training at least one machine learning system using the input data, the sensor data, and annotated video data, wherein the annotated video data is generated by annotating the video data using procedure data;

executing the at least one machine learning system in real time to determine probability of failure of the surgical instrument; and displaying a warning on at least one of the display of the surgical console or a display of the control tower in response to probability of failure of the surgical instrument exceeding a threshold.

14. The method according to claim 13, wherein the at least one machine learning system is a neural network.

15. The method according to claim 14, further comprising:

training the neural network using at least one of supervised training, unsupervised training, or reinforcement learning.

16. The method according to claim 13, further comprising:

comparing the probability of failure of the surgical instrument to a threshold.

17. The method according to claim 16, further comprising:

outputting at least one of an audio or video indication in response to the probability of failure of the surgical instrument exceeding the threshold.

18. The method according to claim 17, further comprising:

disabling the surgical instrument in response to the probability of failure of the surgical instrument exceeding the threshold.

* * * * *